(12) United States Patent
Heinrich et al.

(10) Patent No.: US 7,731,936 B2
(45) Date of Patent: Jun. 8, 2010

(54) METAL COMPLEXES BASED ON TETRATHIOL LIGANDS AND THEIR USE IN NUCLEAR MEDICAL DIAGNOSTICS AND ENDORADIONUCLIDE THERAPY AND METHOD FOR PRODUCING SAID METAL COMPLEXES

(75) Inventors: Tobias Heinrich, Obercunnersdorf (DE); Bernd Johannsen, Dresden (DE); Hans-Juergen Pietzsch, Heidenau (DE); Sepp Seifert, Dresden (DE); Hartmut Spies, Dresden (DE)

(73) Assignee: Forschungszentrum Rossendorf E,V, Dresden (DE)

( * ) Notice: Subject to any disclaimer, the term of this patent is extended or adjusted under 35 U.S.C. 154(b) by 416 days.

(21) Appl. No.: 11/579,575

(22) PCT Filed: Apr. 28, 2005

(86) PCT No.: PCT/DE2005/000868

§ 371 (c)(1),
(2), (4) Date: Mar. 2, 2007

(87) PCT Pub. No.: WO2005/108330

PCT Pub. Date: Nov. 17, 2005

(65) Prior Publication Data

US 2008/0279770 A1    Nov. 13, 2008

(30) Foreign Application Priority Data

May 6, 2004    (DE) .................. 10 2004 022 461

(51) Int. Cl.
*A61K 51/00* (2006.01)
*C07F 13/00* (2006.01)

(52) U.S. Cl. .................. 424/1.65; 534/14; 534/10
(58) Field of Classification Search ............. 424/1.65; 534/14, 10
See application file for complete search history.

(56) References Cited

U.S. PATENT DOCUMENTS 5,175,256 A    12/1992    Kasina et al.
6,368,621 B1    4/2002    Engel et al.

FOREIGN PATENT DOCUMENTS

| DE | 10 2004 022 461 | 12/2005 |
|---|---|---|
| EP | 0344724 | 12/1989 |
| EP | 1072198 | 1/2001 |
| WO | WO-92/05804 | 4/1992 |

OTHER PUBLICATIONS

Anderson et al., CAS: 148:375578.*
Jan. 1, 2003 New routes to bioconjugates of rhenium using the oxobis(dithiolato)rhenate(v)core Uzma Choudhry et al. The Royal Society of Chemistry pp. 311-317.
Jul. 19, 2000 Simple New Method for Effective Concentration of I88Re Solutions from Alumina-Based 188W-188Re Generator Stefan Guhlke et al. The Journal of Nuclear Medicine vol. 41, No. 7 pp. 1271-1278.

* cited by examiner

Primary Examiner—Rei-tsang Shiao
(74) Attorney, Agent, or Firm—Jordan and Hamburg LLP

(57) ABSTRACT

Provided are radiolytically and metabolically stable metal complexes based on tetrathiol ligands useful for nuclear medical diagnostics and in endoradionuclide therapy. Methods for their preparation are also provided. The complexes can have a central ligand, Y, that can be $^{99m}$TcO, $^{186}$ReO, $^{188}$ReO, $^{99m}$TcN, $^{186}$ReN or $^{188}$ReN.

6 Claims, No Drawings

METAL COMPLEXES BASED ON TETRATHIOL LIGANDS AND THEIR USE IN NUCLEAR MEDICAL DIAGNOSTICS AND ENDORADIONUCLIDE THERAPY AND METHOD FOR PRODUCING SAID METAL COMPLEXES

BACKGROUND OF THE INVENTION

The invention relates to the field of radiopharmaceuticals, in particular metal complexes of tetrathiol ligands and their use as radioactive pharmaceuticals for diagnostics and in endoradionuclide therapy and a method for producing said metal complexes.

Diagnostics with technetium 99m preparations are widely used for investigating the renal and hepatobiliary systems, the skeleton, the myocardium, and the brain. Radium isotopes are of interest for therapeutic use in endoradionuclide therapy. The β-emitting isotope $^{188}$Re ($e_{max}$=2.12 MeV) is an attractive radioisotope for radiotherapy and radioimmunotherapy because, apart from its therapy-relevant radiation properties, it can easily be obtained carrier-free as perrhenation (ReO$_4$) in aqueous solution from a $^{188}$W/$^{188}$Re generator system [Guhlke S, Beets A L, Oetjen K, Mirzadeh S, Biersack H J, Knapp F Jr. *Simple new method for effective concentration of $^{188}$Re solutions from alumina-based $^{188}$W-$^{188}$Re generator. J, Nucl Med.* 2000, 41(7):1271-8.]. Because of the long life of the generator, $^{188}$Re is available at low cost for routine preparation of radiopharmaceuticals for treatment for instance of tumors. Regardless thereof, in the past there have been only a limited number of rhenium preparations such as $^{186}$Re-DMSA, $^{186}$Re-DTPA, and $^{186}$Re-diphosphonate for endoradionuclide therapy. However, these compounds are inadequate for therapeutic use because their action is too nonspecific.

Another limiting factor in the development of rhenium radiopharmaceuticals is the lack of suitable complex formers with which the radioactive metal can be stably coupled to biomolecules. In particular, the stability of many rhenium chelates is inadequate for therapeutic application in terms of hydrolysis, reoxidation to perrhenate and radiolysis, which occurs while releasing the radioactive metal from target-forming radiopharmacons.

Derivatives of dimercaptosuccinic acid have been suggested as agents for marking proteins and antibodies with technetium-99 and rhenium-186 or rhenium-188 (U.S. Pat. No. 5,175,256, 1992). This approach does not lead to clearly defined compounds either.

With regard to the aforesaid stability criteria, the described systems and also other systems do not satisfy the requirements for a broad in vivo application.

The object of the invention is to suggest radiolytically and metabolically stable metal complexes that are suitable for conjugation with biomolecules and to suggest a method for their production.

SUMMERY OF THE INVENTION

According to the invention there are provided compounds Which are metal complexes based on Tetrathiol ligands with the formula

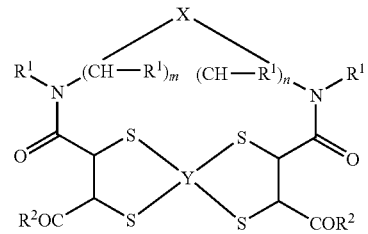

wherein
(CH—R$^1$) stands for substituted or unsubstituted methylene bridges and
r$^1$ represent H, substituted or unsubstituted alkyl groups or substituted or unsubstituted aryl groups, m and n represent the number of methylene groups, whereby the sum of m and n is between 4 and 10,
R$^2$ stands for H, OR$^1$ or NHR$^1$.
Y means 4 times H, $^{99m}$TcO, $^{186}$ReO, $^{188}$ReO, $^{99}$TcN, $^{186}$ReN, or $^{188}$ReN,
X stands for (CH)$_2$, the unsubstituted amino group (N-H) or substituted amino group (N-Z), the guanidvi unit

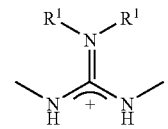

or the urea group

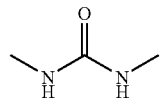

wherein
Z means —(CH—R$^1$)-A, p stands for the number of methylene groups and is between 2 and 8,
A represents a couplable unit, e.g. COOH. COR$^3$, —NCS, and
R$^3$ stands for OH, OR$^1$ or NHR$^1$.

According to further aspects of the invention, methods are provided for preparing the compounds, and the compounds are used for binding radiometals, preferably technetium and rhenium, to biomolecules. The compounds are useful in nuclear medicine and for endordadionuclide therapy.

An important feature for the inventive compounds is that they have improved chemical and radiolytic stability compared to the known DMSA complexes with technetium and rhenium. Furthermore, using a special embodiment of the complex former, the formation of isomers can be intentionally controlled instead of the statistical isomer distribution in the known DMSA complexes.

For attaining the object, dimercaptosuccinic acid (DMSA) is used as a good complex former for technetium and rhenium. The general synthesis strategy is depicted in scheme 1.

By bridging two separate DMSA molecules using a modified carbon chain, a new complex former is synthesized that contains four mercapto groups capable of coordination on one metal atom, and this is converted to the appropriate complex with technetium (V) or rhenium (V). The length of the carbon chain is selected such that the mercapto groups are favorably sterically arranged with respect to the metal. An electron acceptor group (X) is built into the carbon chain and overall it further stabilizes the complex due to interaction with the metal oxogroup or the metal nitride group. The formation of isomers can be intentionally controlled in this manner and using the selection of the chain length. Coupling of biologically active units occurs either using the electron acceptor group (X) or using the carboxyl groups (COOR).

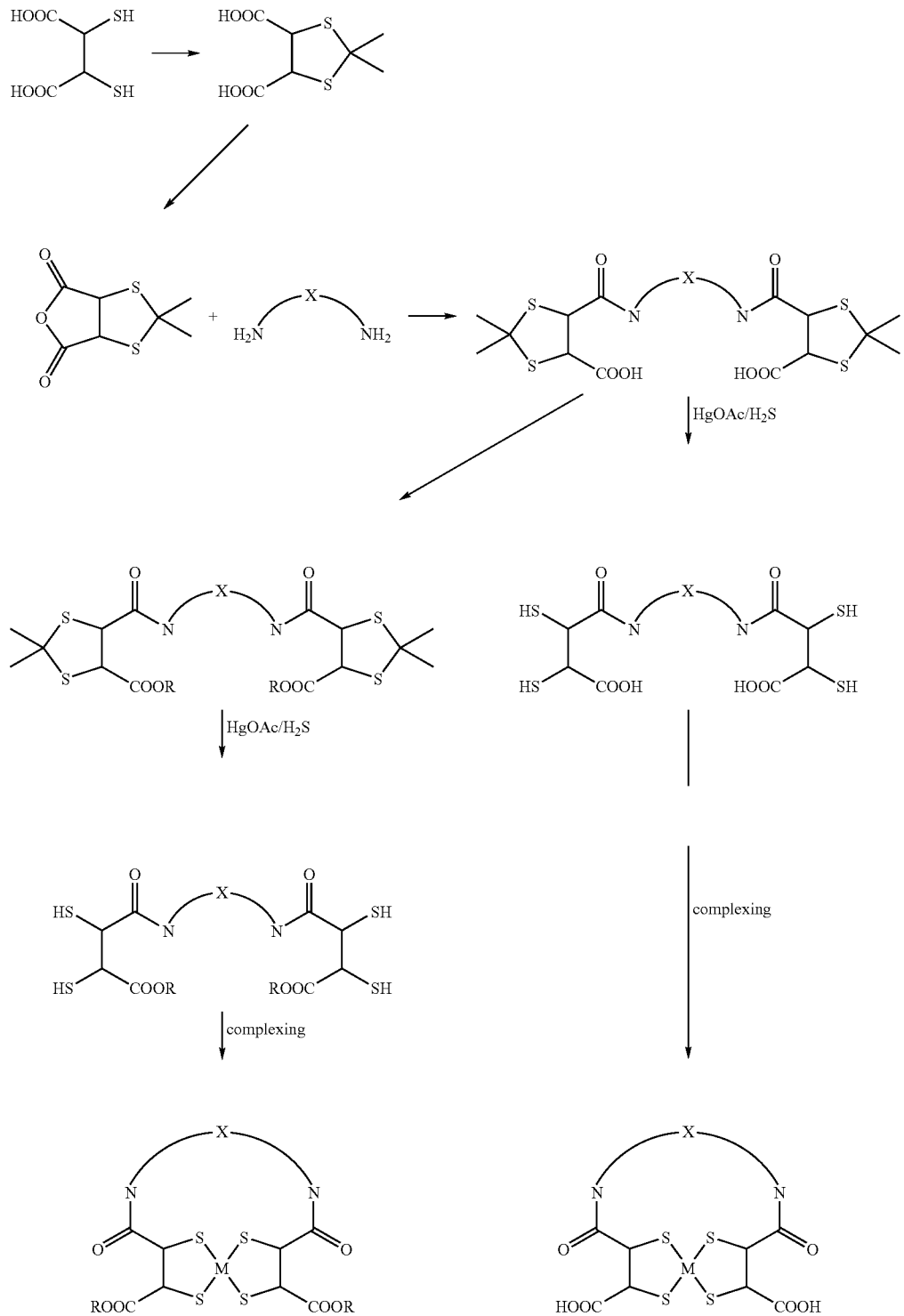

Scheme 1

The method for producing the DMSA-bridged technetium and rhenium complexes is described in greater detail in the following using special examples.

EXAMPLE 1

4,4'-(octane-1,8-diyldiimino)bis(2,3-dimercapto-4-oxobutanoic acid) (4)

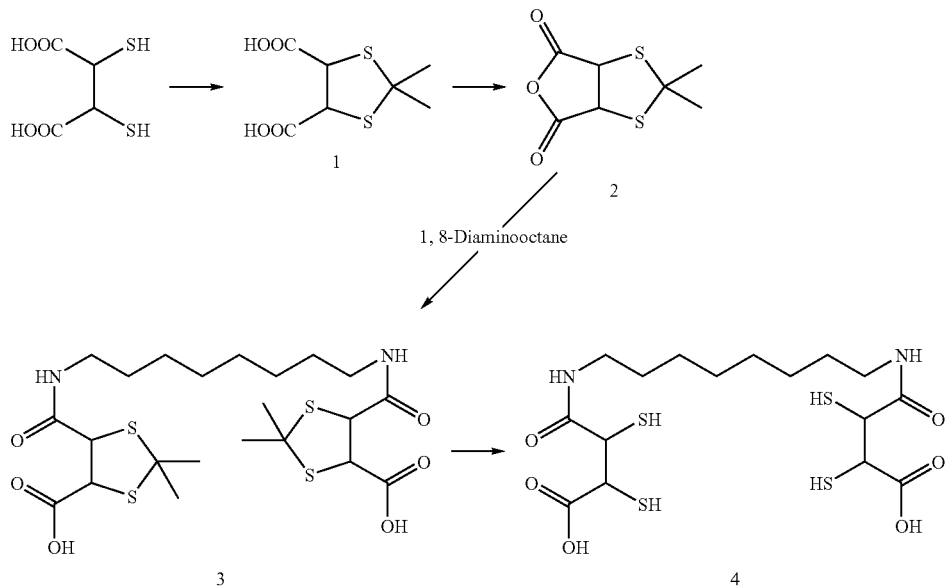

2,2-dimethyl-[1,3]dithiolane-4.5-dicarbonic acid (1)

5.5 mmol (1 g) meso-DMSA are suspended in 20 mL dry acetone. Under ice cooling, the suspension is saturated with $HCl_{(g)}$. After approx. 2 hours of gas introduction and after stirring overnight at RT, (room temperature), the solution is red-brown in color. An alkaline pH for the reaction mixture is adjusted using saturated potassium carbonate solution. At the neutral point the color changes from red to yellow and the potassium salt precipitates out as a light yellow solid. This is left in the aqueous phase and is washed three times with ether. Then conc. hydrochloric acid is added to the aqueous phase until the acid pH range is attained. The potassium salt dissolves and the free acid is extracted from the aqueous phase with ether. The combined ether extracts are derived using sodium sulfate and the solvent is removed in the vacuum. The raw product precipitates as a light brown solid. By heating in benzene under reflux conditions, any impurities present dissolve. The acid is suctioned off and 665 mg of 1 (60%) are obtained as a white solid (solidification point: 150-160° C.).

2,2-dimethyl-dihydro-[1,3]dithiolo[4,5-c]furane-4,6-dione (2)

2.3 mmol (500 mg) 2.2-dimethyl-[1,3]dithiolane-4,5-dicarbonic acid 1 are suspended in acetyl chloride and heated for 1 h under reflux conditions. After cooling to room temperature, by adding 5 ml n-hexane the resultant anhydride 2 is precipitated out. The product is suctioned off, washed with n-hexane, and 1.54 mmol (319 mg) of 2 are obtained as a white solid (solidification point: 138-140° C.).

Under ice cooling and a protective gas atmosphere, 2.44 mmol (500 mg) 2 are dissolved in 12 ml dichloromethane, then 1.5 mmol (306 mg) 1.8 diaminooctane dissolved in 1 ml dichloromethane are slowly added to the reaction mixture by means of syringe and the reaction product precipitates out as a light yellow solid. Stirring is performed for another hour at room temperature and then the resultant solid is suctioned off. After drying, 680 mg (quantitative yield) 3 are obtained as light yellow solid (solidification point: 115-118° C.).

1.4 mmol (776 mg) 3 are placed in 50 ml acetonitrile/$H_2O$ (4:1) at room temperature and under nitrogen and 4.2 mmol (1143 mg) $HgCl_2$, dissolved in 10 ml acetonitrile/$H_2O$, are slowly added to the reaction mixture. After stirring overnight, the resultant light yellow solid is filtered off and dried. Then it is suspended in 50 ml methanol and a uniform $H_2S$ stream is fed in for one hour. The solid gradually dissolves and HgS precipitates out. After one hour the $H_2S$ stream being added is terminated and there is stirring for another hour. Then the black precipitate is filtered off and washed with MeOH. The solvent is removed in the vacuum and 500 mg (76%) 4 are obtained as colorless oil.

$^1$H-NMR (DMSO)/399.95 MHz: δ=1.70 (s, 3H, $CH_3$), 1.73 (s, 3H, $CH_3$), 2.74-2.99 (m, 4H, 4H, 2 $CH_2$—NH), 3.29-3.39 (m, 4H, 2 $CH_2$—NH—C=O), 4.39-4.44 (m, 2H, 2 CH—S), 4.78-4.83 (m, 2H, CH—S), 8.13 (t, $^3$J=5.6 Hz, 2H, 2 O=C—NH)

MS: pos. ESI: [M+H]$^+$, m/z 473.1; neg. ESI: [M−H]$^-$, m/z 470.9

EXAMPLE 2

4,4'-[iminobis(ethane-2,1-diylimino)]bis(2,3-dimercapto-4-oxobutanoic acid) (6)

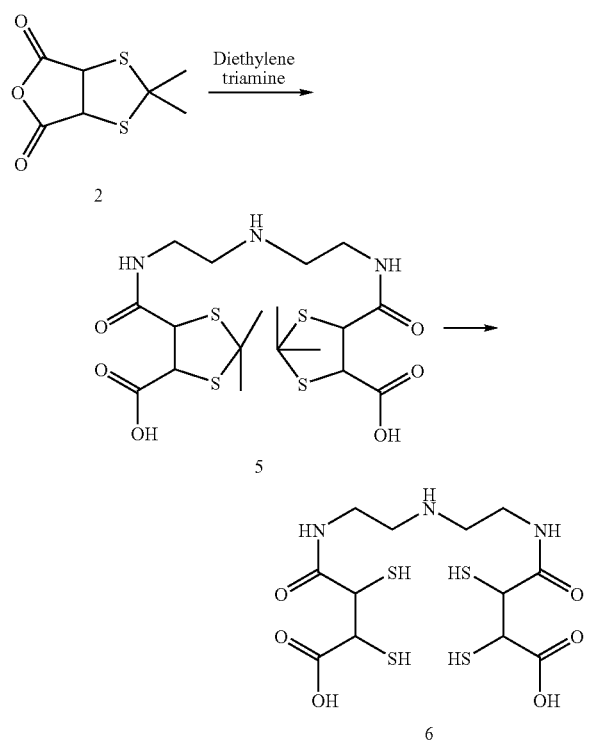

Under ice cooling and a protective gas atmosphere, 2.45 mmol (500 mg) 2 are dissolved in 12 ml dichloromethane, then 1.5 mmol (155 mg) diethylene triamine dissolved in 1 ml dichloromethane are slowly added to the reaction mixture by means of a syringe and the reaction product immediately precipitates out as a light yellow solid. There is stirring for another hour at room temperature and then the resultant solid is suctioned off. After drying, 630 mg (quantitative yield) 5 are obtained as light yellow solid (solidification point: 120-124° C.).

0.66 mmol (341 mg) 5 are placed in 10 ml acetonitrile/$H_2O$ (4:1) at room temperature and under nitrogen and 2 mmol (543 mg) $HgCl_2$ dissolved in 10 ml acetonitrile/$H_2O$ (3:1) are slowly added to the reaction mixture. After stirring overnight, the resultant light yellow solid is filtered off and dried. Then it is suspended in 20 ml methanol and a uniform $H_2S$ stream is fed in for one hour. The solid gradually dissolves and HgS precipitates out. After one hour the $H_2S$ stream being added is terminated and there is stirring for another hour. Then the black precipitate is filtered off and washed with MeOH. The solvent is removed in the vacuum and 80 mg (30%) 6 are obtained as a white solid (solidification point: 70-90° C.).

$^1$H-NMR (DMSO)/399.95 MHz: δ=1.70 (s, 3H, $CH_3$), 1.73 (s, 3H, $CH_3$), 2.74-2.99 (m, 4H, 4H, 2 $CH_2$—NH), 3.29-3.39 (m, 4H, 2 $CH_2$—NH—C=O), 4.39-4.44 (m, 2H, 2 CH—S), 4.78-4.83 (m, 2H, CH—S), 8.13 (t, $^3$J=5.6 Hz, 2H, 2 O=C—NH)

MS: pos. ESI: $[M+H]^+$, m/z 431.8; neg. ESI: $[M-H]^-$, m/z 429.8

EXAMPLE 3

4,4$^1$-[iminobis(propane-3,1-diylimino)]bis(2,3-dimercapto-4-oxobutanoic acid) (8)

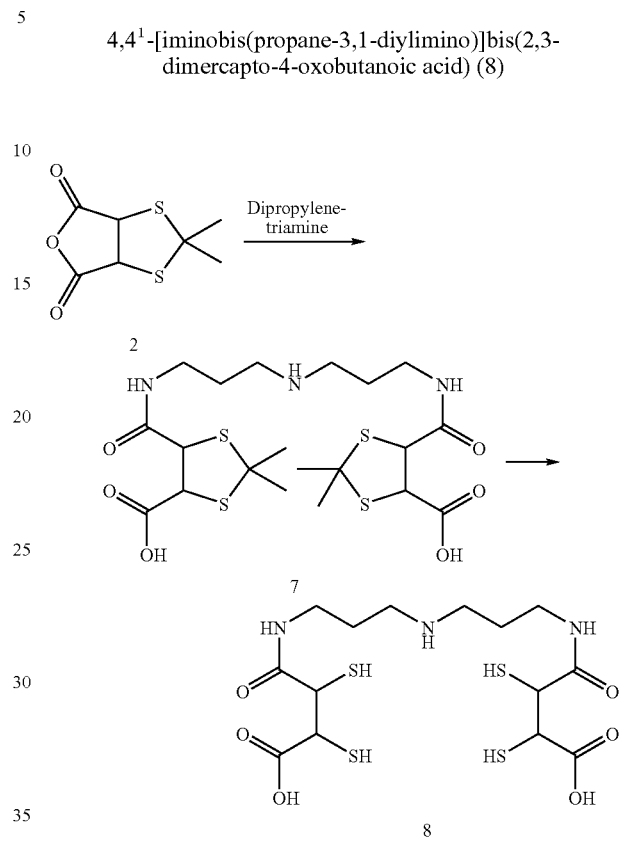

Under ice cooling and a protective gas atmosphere, 1.47 mmol (300 mg) 2 are dissolved in 20 ml dichloromethane, then 0.75 mmol (96 mg) dipropylene triamine dissolved in 1 ml dichloromethane are slowly added to the reaction mixture by means of a syringe and the reaction product immediately precipitates out as a light yellow solid. There is stirring for another hour at room temperature and then the resultant solid is suctioned off. After drying, 395 mg (quantitative yield) of 7 are obtained as light yellow amorphous product.

0.74 mmol (394 mg) 7 are placed in 30 ml acetonitrile/$H_2O$ (3:1) at room temperature and 7.4 mmol (2 g $HgCl_2$) dissolved in 30 ml acetonitrile/$H_2O$ (3:1) are slowly added to the reaction mixture. After stirring overnight, the resultant light yellow solid is left in the flask and the solvent is removed in the vacuum. Then the entire residue is rinsed out of the flask with a lot of water, the solid is filtered off and dried. Then it is suspended in 70 ml methanol and a uniform $H_2S$ stream is fed in for one hour. After one hour the $H_2S$ stream being added is terminated and there is stirring over the weekend. Then the black precipitate is filtered off and washed with MeOH, the solvent is removed in the vacuum, and 80 mg (30%) 8 are obtained as a white solid (Solidification point: 70-90° C.).

$^1$H-NMR (DMSO)/399.95 MHz: δ=1.70 (s, 3H, $CH_3$), 1.73 (s, 3H, $CH_3$), 2.74-2.99 (m, 4H, 4H, 2 $CH_2$—NH), 3.29-3.39 (m, 4H, 2 $CH_2$—NH—C=O), 4.39-4.44 (m, 2H, 2 CH—S), 4.78-4.83 (m, 2H, CH—S), 8.13 (t, $^3$J=5.6 Hz, 2H, 2 O=C—NH)

$^{13}$C-NMR (acetone)/100.57 MHz: δ=34.5 (2 $CH_3$), 57.3 (2 CH—S), 65.6 (S—C—S), 171.0 (2 O—C=O)

MS: pos. ESI: $[M+H]^+$, m/z 431.8; neg. ESI: $[M-H]^-$, m/z 429.8

EXAMPLE 4

Methyl-4,5,17,18-tetramercapto-3,6,16-trixo-2-oxa-7,11,15-triazanonadecane-19-oat (10)

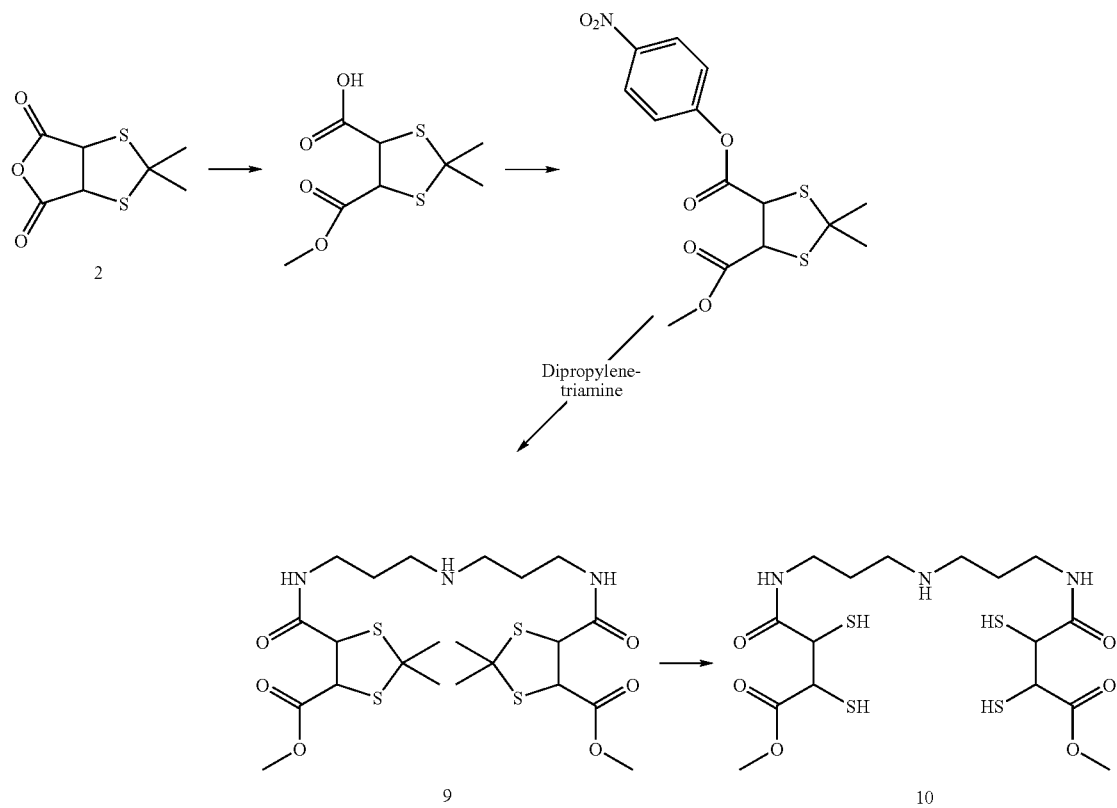

Under reflux conditions, 4.9 mmol (1000 mg) 2 are heated in 40 ml methanol. The reaction is controlled by means of DC. Then the solvent is removed in the vacuum. 1150 mg (quant.) of the half-ester are obtained as a brown oil, and this is used further without purification.

5.3 mmol (1250 mg) half-ester, 5.3 mmol (738 mg) p-nitrophenol, and 5.3 mmol 1094 mg) DCC are dissolved in 75 ml ethyl acetate at room temperature and stirred overnight, the white solid (DHU) is filtered off, and the residual mother liquid is concentrated in the vacuum. The oily product is purified with an n-hexane/ether eluent mixture (2:1) using silica gel. After dissolving in an n-hexane/ether mixture (5:2) and subsequent crystallization of the product, 450 mg (25%) of the p-nitrophenyl ester are obtained as a white solid (solidification point: 87-90° C.).

0.14 mmol (50 mg) of the p-nitrophenyl ester are dissolved in 5 ml toluene at room temperature. Then 0.14 mmol (25 mg) dipropylene triamine dissolved in 1 ml toluene are slowly added to the reaction mixture. When the amine is added a bright yellow byproduct precipitates out immediately. The reaction is controlled by means of DC and terminates after approx. 1 h. The yellow solid is filtered off and the residual mother liquid is concentrated in the vacuum. 71 mg (89%) 9 are obtained as yellow oil.

0.46 mmol (350 mg) 9 are provided in 20 ml acetonitrile/$H_2O$ (3:1) at room temperature and 4.6 mmol (1250 mg) $HgCl_2$ dissolved in 20 ml acetonitrile/$H_2O$ (3:1) are slowly added to the reaction mixture. The initially orange-colored clear solution becomes milky and turbid. After stirring overnight, the solvent mixture is removed in the vacuum. The resultant white solid is washed well with water and then dried. The dry Hg complex (960 mg) is suspended in 50 ml MeOH and a uniform $H_2S$ stream is fed in for one hour. The white solid gradually dissolves and a black precipitate precipitates out. After one hour the $H_2S$ stream being added is terminated and there is stirring for another hour. Then the black precipitate is filtered off and washed with MeOH, the solvent is removed in the vacuum, and 240 mg (83%) 10 are obtained as a pale yellow oil.

MS: pos. ESI: [M+H]$^+$, m/z 488.77; neg. ESI: [M−H]$^−$, m/z 486.11

EXAMPLE 5

$N^2,N^2$-(iminodipropane-3,1,diyl)bis($N^4,N^4$-diisobutyl-2,3-dimercaptosuccinamide) (14)

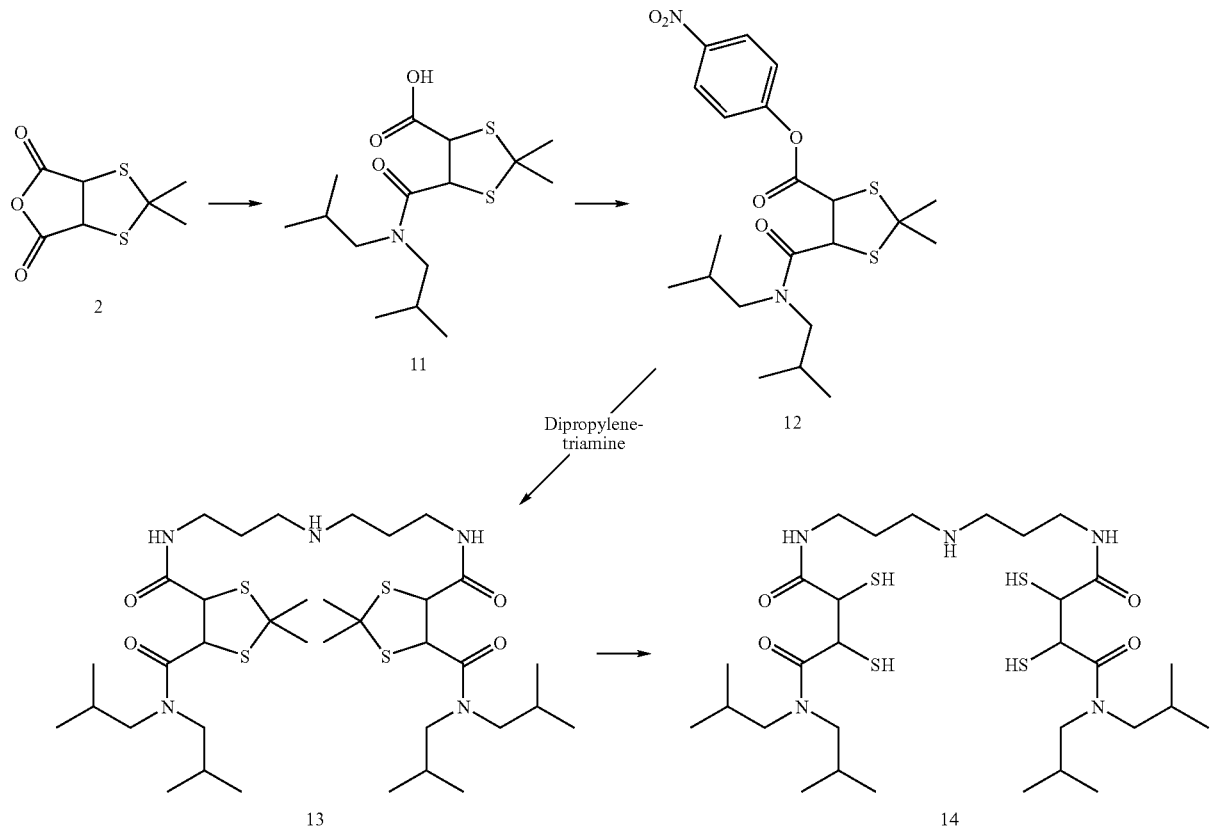

Under ice cooling and a protective gas atmosphere, 2.45 mmol (500 mg) 2 are dissolved in 12 ml dichloromethane, then 3.7 mmol (475 mg) diisobutylamine dissolved in 2 ml dichloromethane are slowly added to the reaction mixture by means of a syringe. The reaction is controlled by means of DC and is terminated after 3 h. The solvent is removed in the vacuum, the residue solidifying suddenly at the end. The raw product is dissolved in a little ethanol and 10-percent hydrochloric acid is added while stirring until turbidity occurs. The compound precipitates out in the refrigerator. After filtering out and drying 510 mg (70%) 11 are obtained as a light pink-colored solid (solidification point: 148-150° C.).

05.9 mmol (200 mg) 11, 0.6 mmol (84 mg) p-nitrophenol, and 0.59 mmol 122 mg) DCC are dissolved in 10 ml ethyl acetate at room temperature. Stirring is performed at room temperature, an orange/brown suspension resulting from the light gray suspension. After 1-2 h, the white solid (DHU) is filtered off, and the residual mother liquid is concentrated in the vacuum. The oily product is purified with an n-hexane/ether eluent mixture (1:1) using silica gel, and 199 mg (75%) 12 are obtained as a white solid (solidification point: 87-90° C.).

0.93 mmol (420 mg) 12 are dissolved in 25 ml toluene at room temperature. Then 0.93 mmol (122 mg) dipropylene triamine dissolved in 1 ml toluene are slowly added to the reaction mixture. When the amine is added a bright yellow byproduct precipitates out immediately. The reaction is controlled by means of DC and terminates after approx. 1 h. The yellow solid is filtered off and the residual mother liquid is concentrated in the vacuum. 350 mg (95%) 13 are obtained as pale yellow oil that is used further without purification.

0.46 mmol (350 mg) 13 are provided in 20 ml acetonitrile/$H_2O$ (3:1) at room temperature and 4.6 mmol (1250 mg) $HgCl_2$ dissolved in 20 ml acetonitrile/$H_2O$ (3:1) are slowly added to the reaction mixture. The initially orange-colored clear solution becomes milky and cloudy. After stirring overnight, the solvent mixture is removed in the vacuum. The resultant white solid is washed well with water and then dried. The dry Hg complex (960 mg) is suspended in 50 ml MeOH and a uniform $H_2S$ stream is fed in for one hour. The white solid gradually dissolves and a black precipitate precipitates out. After one hour the $H_2S$ stream being added is terminated and there is stirring for another hour. Then the black precipitate is filtered off and washed with MeOH, the solvent is removed in the vacuum, and 290 mg (92%) 14 are obtained as a pale yellow oil.

$^1$H-NMR ($CDCl_3$)/399.95 MHz: δ=0.83-0.86 (m, 12H, 4 $CH_3$—CH), 0.90-0.93 (m, 12H, 4 $CH_3$—CH), 1.60-1.68 (m, 4H, 2 $CH_2$—$CH_2$—$CH_2$), 1.81 (s, 3h, $CH_3$), 18.85 (s, 3H, $CH_3$), 1.91-2.00 (m, 4H, 4$CH_3$—CH—$CH_3$), 2.61-2.66 (m, 4H, $CH_2$—NH—$CH_2$), 3.00-3.10 (m, 6H, 4 $CH_3$—CH—$CH_2$, 2 $CH_2$—NH—C=O), 3.21-3.31 (m, 6H, 4 $CH_3$—CH—$CH_2$, 2 $CH_2$—NH—C=O), 4.64 (d, $^3$J=5.6 Hz, 2H, CH—S, 4.88 (d, $^3$J=5.6 Hz, 2H, CH—S

MS: pos. ESI: [M+H]⁺, m/z 682.57; neg. ESI: [M−H]⁻, m/z 680.31

EXAMPLE 6

9-(ethylimino)-2,3,15,16-tetramercapto-4,14-dioxo-5,8,10,13-tetraazaheptadecane-1,17-dionic acid (17)

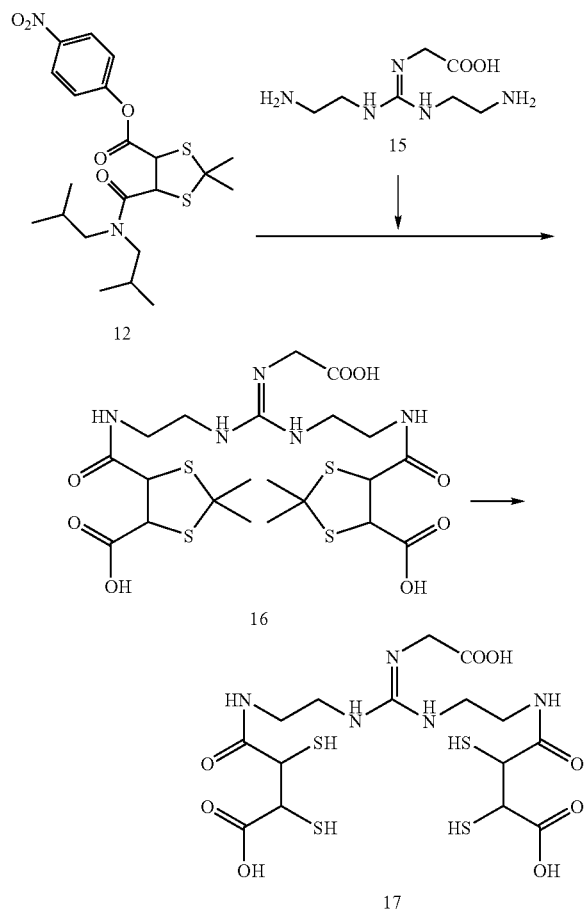

0.93 mmol (420 mg) 12 are dissolved in 25 ml toluene at room temperature. Then 0.93 mmol (122 mg) 15 (synthesized according to V. A. Vallaincourt et. al., J. Med. Chem. 44, 2001, 1231) dissolved in 1 ml toluene are slowly added to the reaction mixture. When the amine is added, a bright yellow byproduct immediately precipitates out. The reaction is controlled by means of DC and is terminated after approx. 2 h. The yellow solid is filtered off and the residual mother liquid is concentrated in the vacuum. 250 mg (75%) 16 are obtained as a pale yellow oil that is used further without purification.

0.46 mmol (350 mg) 16 are provided in 20 ml acetonitrile/H₂O (3:1) at room temperature and 4.6 mmol (1250 mg) HgCl₂ dissolved in 20 ml acetonitrile/H₂O (3:1) are slowly added to the reaction mixture. The initially orange-colored clear solution becomes milky and turbid. After stirring overnight, the solvent mixture is removed in the vacuum. The resultant white solid is washed well with water and then dried. The dry Hg complex (960 mg) is suspended in 50 ml MeOH and a uniform H₂S stream is fed in for one hour. The white solid gradually dissolves and a black precipitate precipitates out. After one hour the H₂S stream being added is terminated and there is stirring for another hour. Then the black precipitate is filtered off and washed with MeOH, the solvent is removed in the vacuum, and 300 mg (90%) 17 are obtained as a pale yellow oil.

MS: pos. ESI: [M+H]⁺, m/z 532.57; neg. ESI: [M−H]⁻, m/z 530.61

EXAMPLE 7

4-nitrophenyl-4-(bis{3-[({5-[(diisobutylamino)carbonyl]-2,2-dimethyl-1,3-dithiolane-4-yl}carbonylamino]propyl}amino)-4-oxobutanoate (19)

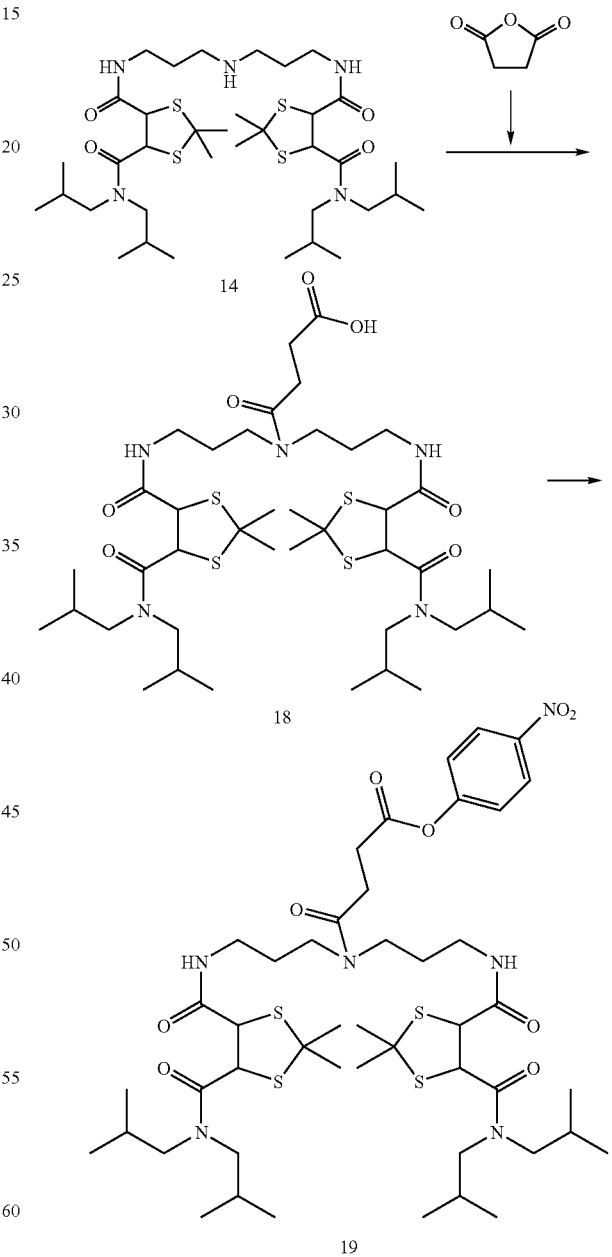

0.25 mmol (200 mg) 14 are dissolved in 30 ml dichloromethane and 0.9 mmol succinic acid anhydride are added. 30 drops TEA are added as base. Stirring is performed at room temperature. The reaction is controlled by means of DC and is terminated after 2-3 h. The solvent is removed in the vacuum. The oily product is purified with a chloroform/ether eluent mixture (10:1) using silica gel, and 130 mg (60%) 18 are obtained as a colorless oil.

0.14 mmol (117 mg) 18, 0.14 mmol (20 mg) p-nitrophenol, and 0.14 mmol (30 mg) DCC are dissolved in 25 ml ethyl acetate at room temperature. Stirring is performed at room temperature, an orange-brown suspension resulting from the light gray suspension. After 1-2 h, the white solid (DHU) is filtered off and the residual mother liquid is concentrated in the vacuum. The oily product is purified with a chloroform/acetone eluent mixture (2:1) using silica gel, and 157 mg (75%) 19 are obtained.

MS: pos. ESI: [M+H]$^+$, m/z 983.8; neg. ESI: [M+H]$^+$, m/z 1005.8

EXAMPLE 8

Coupling the Model Peptide gly-gly-gly

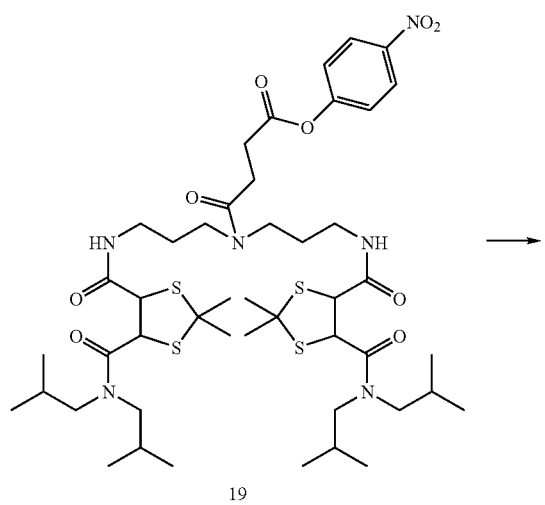

19

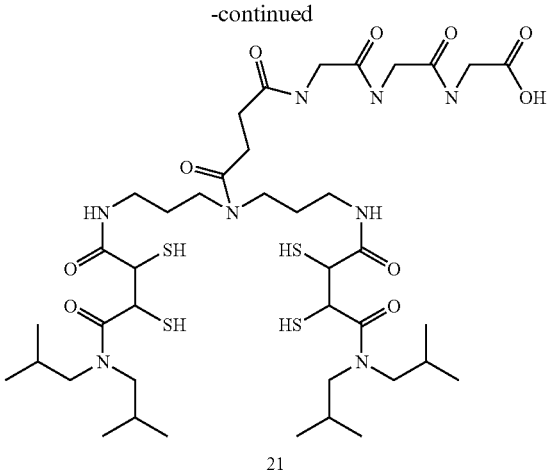

21

0.1 mmol (105 mg) 19 are provided in 5 ml acetonitrile/H$_2$O (3:1) at room temperature and 1.0 mmol (290 mg) HgCl$_2$ dissolved in 5 ml acetonitrile/H$_2$O (3:1) are slowly added to the reaction mixture. The initially orange-colored clear solution becomes milky and turbid. After stirring overnight, the solvent mixture is removed in the vacuum. The resultant white solid is washed well with water and then dried. The dry Hg complex (180 mg) is suspended in 50 ml acetonitrile/H$_2$O (3:1) and a uniform H$_2$S stream is fed in for one hour. The white solid gradually dissolves and a black precipitate precipitates out. After one hour the H$_2$S stream being added is terminated and there is stirring for another hour. Then the black precipitate is filtered off using cellite and washed with acetonitrile/H$_2$O (3:1), the solvent is removed in the vacuum, and 79 mg (88%) 20 are obtained as a powdery substance.

6.6 µmol (6 mg) 20 are provided in 5 ml acetonitrile/H$_2$O (3:1) at room temperature and 6.6 µmol (1.3 mg) Gly-Gly-Gly dissolved in 5 ml acetonitrile/H$_2$O (3:1) are slowly added to the reaction mixture. After 2 h of stirring at room temperature, the solvent mixture is removed in the vacuum and 7 mg 21 are obtained as a light green powdery substance.

MS: pos. ESI: [M+H]$^+$, m/z 953.5

EXAMPLE 9

Oxorhenium(V) Complex of the tetrathiol ligand (14)

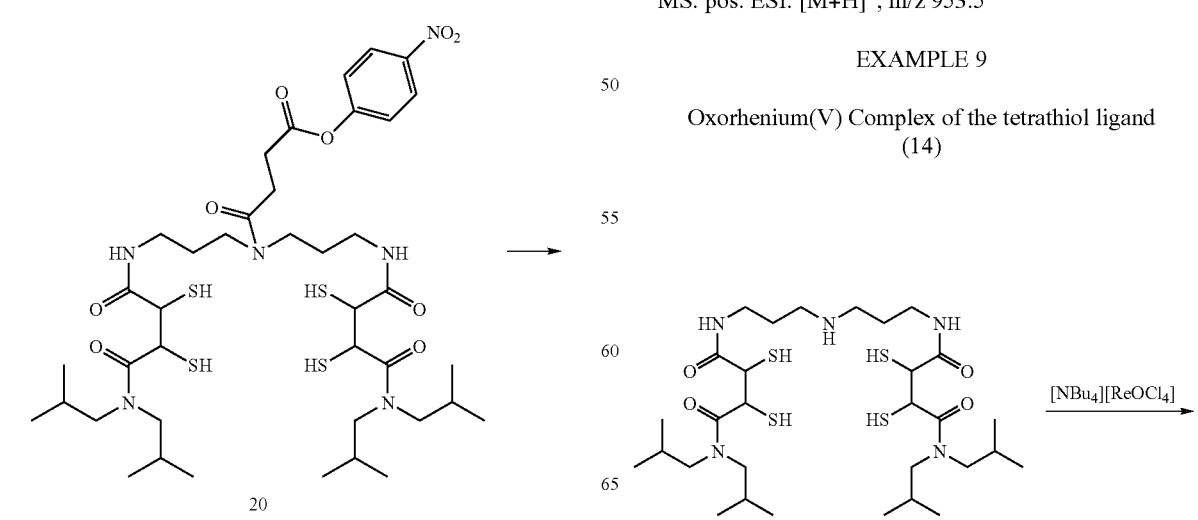

20

-continued

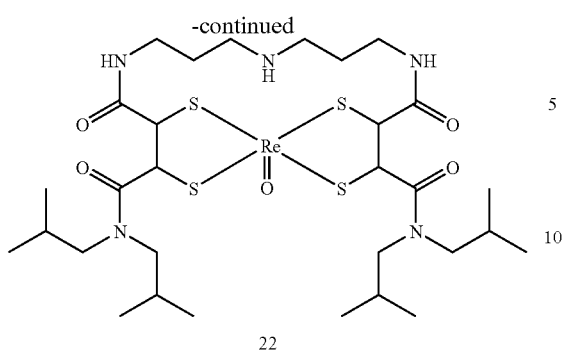

22

0.15 mmol (88 mg) [NBu$_4$][ReOCl$_4$] are provided in 100 ml dry MeOH at room temperature. While stirring, 0.15 mmol (100 mg) 14 dissolved in 100 ml MeOH are slowly added to the reaction mixture. The color of the solution changes from green to orange-brown. The reaction is controlled by means of DC and terminates after 1-2 h. The solvent is removed in the vacuum and 190 mg raw product are obtained as a brown oil. The oily product is purified with an isopropanol/chloroform/ammonia eluent mixture (5:4:1) using silica gel, and 42 mg (45%) 22 are obtained as an orange colored solid.

$^1$H-NMR (CDCl$_3$)/400.13 MHz: δ=1.15 (s, 3H, 4 CH$_3$), 1.87 (ddd, $^2$J=13.1 Hz, $^3$J=6.3, 6.3 Hz, 1H, CH$_2$—CH$_2$), 2.06 (ddd, $^2$J=13.1 Hz, $^3$J=6.8, 6.8 Hz, 1H, CH$_2$—CH$_2$), 2.30 (dd, $^2$J=13.7 Hz, $^3$J=7.7 Hz, 1H, C—CH$_2$—CH), 2.54 (dd, $^2$J=13.7 Hz, $^3$J=7.7 Hz, 1H, C—CH$_2$—CH), 2.93 (dd, $^3$J=6.8, 6.3 Hz, 2H, CH$_2$—CH$_2$), 5.96 (ddd, $^3$J=15.5, 7.7, 7.7 Hz, 1H, CH=CH—C—S), 6.49 (d, $^3$J=15.5 Hz, 1H, CH=CH—C—S), 6.81-6.92 (m, 2H, 2 aromat. CH), 7.02 (d, $^3$J=4.6 Hz, 1H, 1 aromat. CH), 7.16 (m, 1H, 1 aromat. CH), 7.25 (m, 1H, 1 aromat. CH), 7.40 (m, 1H, aromat. CH), 7.98 (d, $^3$J=7.6 Hz, 1H, CH=C—C=O)

MS: pos. ESI: [M+H]$^+$, m/z 882.46; neg. ESI: [M−H]$^−$, m/z 880.20

EXAMPLE 10

$^{188}$ReO Complex of the tetrathiol ligand (14)

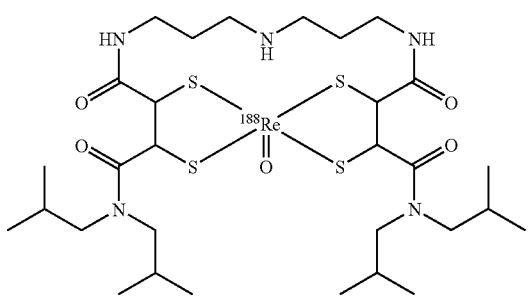

1.0 ml perrhenate generator eluate is added to 1.0 mg ligand 14, dissolved in a mixture of 0.5 ml methanol and 0.2 ml propylene glycol. After adding 1.0 mg SnCl$_2$, dissolved in 0.1 ml 0.1 M HCl, the reaction mixture is maintained 30 min at 100° C. Radiochemical yield approx. 85%.

HPLC Analysis
Column: Zorbax 300 SB-C18 5 μm 9.4×250 mm
Eluents: A: acetonitrile/0.1% TFA, B: water/0.1% TFA
20 min 50% A, in 5 min to 90% A, 6 min 90% A, in 2 min back to 50% A.
Flow: 4 ml/min

EXAMPLE 11

$^{99m}$TcO Complex of the tetrathiol ligand (14)

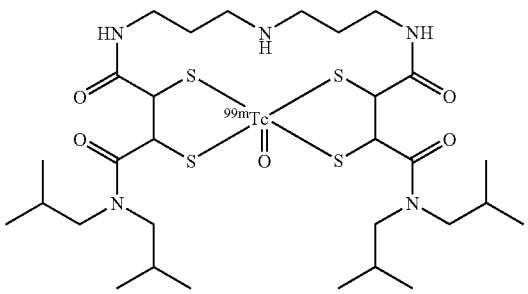

0.2 ml pertechnetate generator eluate are added to 1.0 mg ligand 14 dissolved in a mixture of 0.2 ml methanol, 0.2 ml propylene glycol, and 0.02 ml 1 n NaOH. After adding 0.5 mg SnCl$_2$ dissolved in 0.1 ml methanol, the reaction mixture is maintained 10 min at room temperature. Radiochemical yield approx. 90%.

HPLC Analysis
Column: Zorbax 300 SB-C18 5 μm 9.4×250 mm
Eluents: A: acetonitrile/0.1% TFA, B: water/0.1% TFA
20 min 50% A, in 5 min to 90% A, 6 min 90% A, in 2 min back to 50% A.
Flow: 4 ml/min

EXAMPLE 12

$^{188}$ReN Complex of the tetrathiol ligand (14)

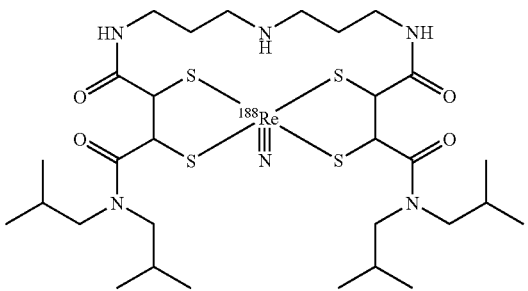

0.5 ml perrhenate generator eluate (10-30 mCi) are added to a mixture of 1.0 mg S-methyl-dithiocarbazate, 0.2 mg SnCl$_2$ (dissolved in 0.5 ml 20% acetic acid), and 28.0 mg sodium oxalate, and is kept at room temperature for 15 min. Then the pH of the reaction mixture is adjusted to 7.0 (1.25 ml 0.5 M sodium carbonate buffer). After the addition of the tetrathiol 14 (1 mg in 0.25 ml methanol), it is heated for 30 min to 70° C. Radiochemical yield approx. 90%.

HPLC Analysis
   Column: Zorbax 300 SB-C18 5 μm 9.4×250 mm
   Eluents: A: acetonitrile/0.1% TFA, B: water/0.1% TFA
   20 min 50% A, in 5 min to 90% A, 6 min 90% A, in 2 min back to 50% A
   Flow: 4 ml/min

EXAMPLE 13

$^{99m}$TcN Complex of the tetrathiol ligand (14)

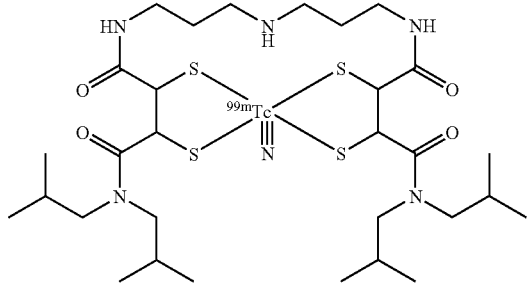

0.5 ml pertechnetate generator eluate (10-30 mCi) are added to a mixture of 1.0 mg S-methyl-dithiocarbazate, 0.2 mg SnCl$_2$ (dissolved in 0.5 ml 20% acetic acid), and 28.0 mg sodium oxalate, and is kept at room temperature for 15 min. Then the pH of the reaction mixture is adjusted to 7.0 (1.25 ml 0.5 M sodium carbonate buffer). After the addition of the tetrathiol 14 (1 mg in 0.25 ml methanol), it is heated for 30 min to 70° C. Radiochemical yield approx. 95%.

HPLC Analysis
   Column: Zorbax 300 SB-C18 5 μm 9.4×250 mm
   Eluents: A: acetonitrile/0.1% TFA, B: water/0.1% TFA
   20 min 50% A, in 5 min to 90% A, 6 min 90% A, in 2 min back to 50% A
   Flow: 4 ml/min

The invention claimed is:

1. Metal complexes based on tetrathiol ligands with the formula

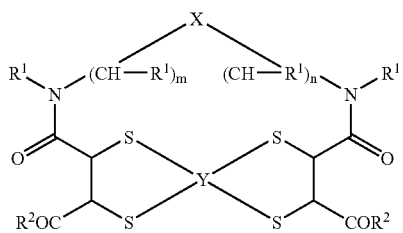

wherein
   each (CH—R$^1$) represents a substituted or unsubstituted methylene-group and each R$^1$ represents H, a substituted or unsubstituted alkyl group or a substituted or unsubstituted aryl group, m and n represent the number of methylene groups and the sum of m and n is between 4 and 10,
   each R$^2$ represents H, OR$^1$ or NHR$^1$,
   Y represents 4 times H, $^{99m}$TcO, $^{186}$ReO, $^{188}$ReO, $^{99m}$TcN, $^{186}$ReN, or $^{188}$ReN,
   X represents (CH)$_2$, an unsubstituted amino group (N—H) or substituted amino group (N-Z), the guanidyl unit

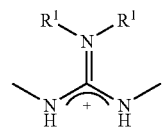

or a urea group

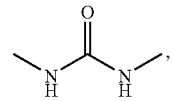

wherein
   Z represents —(CH—R$^1$)$_p$-A, represents the number of methylene groups and is between 2 and 8, and
   A represents a couplable unit.

2. Metal complexes according to claim 1, wherein the couplable unit is selected —COOH, COR$^3$ or —NCS.

3. A nuclear medicine for diagnosis of a patient, comprising a metal complex according to claim 1.

4. A nuclear medicine endoradionuclide therapy of a patient, comprising a metal complex according to claim 1.

5. A method of coupling a biomolecule to a metal complex, comprising coupling a metal complex according to claim 1 to a biomolecule at X or R$^2$ of the metal complex.

6. A method of producing a metal complex of claim 1, comprising reacting meso-dimercapto-succinic acid with a diamine R$^1$HN—(CHR$^1$)$_n$—Y—(CHR$^1$)$_m$—NHR$^1$ to produce a tetrathiol ligand and reacting the tetrathiol ligand with technetium or rhenium.

* * * * *